United States Patent
Imran (10) Patent No.: US 9,949,677 B2
(45) Date of Patent: Apr. 24, 2018

(54) IMPLANTABLE OXIMETRIC MEASUREMENT APPARATUS AND METHOD OF USE

(71) Applicant: Mir Imran, Los Altos Hills, CA (US)

(72) Inventor: Mir Imran, Los Altos Hills, CA (US)

(73) Assignee: InCube Labs, LLC, San Jose, CA (US)

( * ) Notice: Subject to any disclaimer, the term of this patent is extended or adjusted under 35 U.S.C. 154(b) by 575 days.

(21) Appl. No.: 13/657,706

(22) Filed: Oct. 22, 2012

(65) Prior Publication Data

US 2013/0289372 A1    Oct. 31, 2013

Related U.S. Application Data (60) Provisional application No. 61/627,999, filed on Oct. 21, 2011.

(51) Int. Cl.
*A61B 5/1455* (2006.01)
*A61B 5/1459* (2006.01)
*A61B 5/00* (2006.01)

(52) U.S. Cl.
CPC .......... *A61B 5/1459* (2013.01); *A61B 5/0031* (2013.01); *A61B 5/14551* (2013.01);
(Continued)

(58) Field of Classification Search
CPC ..... A61B 5/1459; A61B 5/1495; A61B 5/031; A61B 5/14542; G01N 21/8507
See application file for complete search history.

(56) References Cited

U.S. PATENT DOCUMENTS 5,991,654 A * 11/1999 Tumey et al. .............. 600/479
6,334,856 B1 * 1/2002 Allen et al. ................ 604/191
(Continued)

FOREIGN PATENT DOCUMENTS

JP    2001321362 A    11/2001
JP    2008512202 A    4/2008
(Continued)

OTHER PUBLICATIONS

International search report and written opinion dated Mar. 20, 2013 for PCT/US2012/061394.
(Continued)

*Primary Examiner* — Eric Winakur
*Assistant Examiner* — Marjan Fardanesh
(74) *Attorney, Agent, or Firm* — Wilson Sonsini Goodrich & Rosati; Joel M. Harris, Esq.

(57) ABSTRACT

Embodiments provide an apparatus, system, kit and method for in vivo measurement of blood oxygen saturation (BAS). One embodiment provides an implantable apparatus for measuring BAS comprising a housing, emitter, detector, processor and power source. The housing is configured to be injected through a tissue penetrating device into a target tissue site (TS). The emitter is configured to emit light into the TS to measure BAS, the emitted light having at least one wavelength (LOW) whose absorbance is related to a BAS. The detector is configured to receive light reflected from the TS, detect light at the LOW and generate a detector output signal (DOS) responsive to an intensity of the detected light. The processor is operably coupled to the detector and emitter to send signals to the emitter to emit light and receive the DOS and includes logic for calculating a BAS and generate a signal encoding the BAS.

38 Claims, 9 Drawing Sheets

(52) U.S. Cl.
CPC ........... *A61B 5/6861* (2013.01); *A61B 5/6884* (2013.01); *A61B 2560/063* (2013.01); *A61B 2562/162* (2013.01)

(56) References Cited

U.S. PATENT DOCUMENTS

| | | | |
|---|---|---|---|
| 6,731,962 B1* | 5/2004 | Katarow et al. | 600/323 |
| 7,660,616 B1* | 2/2010 | Poore | 600/341 |
| 7,697,967 B2* | 4/2010 | Stafford | 600/345 |
| 7,813,778 B2* | 10/2010 | Benaron et al. | 600/323 |
| 8,417,305 B2* | 4/2013 | Dixon | 600/323 |
| 2003/0004457 A1 | 1/2003 | Andersson | |
| 2003/0158520 A1* | 8/2003 | Safabash | A61M 5/158 604/116 |
| 2004/0176669 A1 | 9/2004 | Colvin et al. | |
| 2005/0027178 A1* | 2/2005 | Iddan | 600/339 |
| 2007/0027371 A1 | 2/2007 | Benaron et al. | |
| 2008/0121825 A1* | 5/2008 | Trovato | A61N 5/1014 250/506.1 |
| 2009/0076401 A1* | 3/2009 | Mazar | A61B 5/0031 600/508 |
| 2009/0156988 A1 | 6/2009 | Ferren et al. | |
| 2009/0292212 A1 | 11/2009 | Bran et al. | |
| 2010/0114225 A1* | 5/2010 | Imran et al. | 607/9 |
| 2010/0185142 A1 | 7/2010 | Kamen et al. | |
| 2010/0204678 A1* | 8/2010 | Imran | 604/511 |
| 2010/0312188 A1 | 12/2010 | Robertson et al. | |
| 2010/0331868 A1 | 12/2010 | Bardy | |
| 2011/0190600 A1 | 8/2011 | McKenna et al. | |

FOREIGN PATENT DOCUMENTS

| | | | | |
|---|---|---|---|---|
| JP | 2008142296 A | 6/2008 | | |
| JP | 2009544409 A | 12/2009 | | |
| JP | 2010524512 A | 7/2010 | | |
| JP | 2011519703 A | 7/2011 | | |
| WO | WO 2007041584 A2 * | 4/2007 | ............... | A61K 9/22 |
| WO | WO 2009048999 A1 * | 4/2009 | ............... | A61N 1/36 |
| WO | WO 2011119896 A1 * | 9/2011 | ......... | A61B 5/14503 |

OTHER PUBLICATIONS

European search report and search opinion dated Aug. 24, 2015 for EP Application No. 12840942-2.

* cited by examiner

IMPLANTABLE OXIMETRIC MEASUREMENT APPARATUS AND METHOD OF USE

CROSS-REFERENCE TO RELATED APPLICATIONS

This application claims the benefit of priority U.S. Provisional Patent Application No. 61/627,999 filed Oct. 21, 2011; entitled, Implantable Oximetric Measurement Apparatus and Method of Use, which is fully incorporated by reference for all purposes.

FIELD OF THE INVENTION

Embodiments described herein relate to an apparatus, system and method for performing in vivo measurements in the body of a living animal. More specifically, embodiments described herein relate to an apparatus, system and method for performing in vivo oximetry measurements in the body of a human patient.

BACKGROUND

Blood oxygen saturation, herein oxygen saturation is a measurement corresponding to the degree to which the hemoglobin molecule is saturated with oxygen. Oxygen saturation provides a wealth of information about a patient's health including particular conditions. It can, for example, provide information on a person's pulmonary function, cardiovascular function, circulation and hematologic state. The current standard method for measurement of oxygen saturation is a technique known as oximetry. Oximetry is based on the principle that the color of blood is related to the oxygen saturation level ($SaO_2$) in the blood. Oximetric devices use a light source and light dectector. Light from the light source (known as afferent light) is emitted into the patient's blood directly via a catheter or indirectly via a transcutaneous probe placed on the skin. Typically, the light source emits at least two separate wavelengths of light with each wavelength having different absorption curves such that the ratio of the two absorptions is unique for the range of oxygen saturations from 0% through 100% saturation. The detector detects light that is transmitted through the patient's blood known as efferent light. As is explained in more detail below, the nature of the efferent light depends on the blood oxygen saturation sated of the patient's blood. The efferent light can be collected directly from a catheter positioned in the patient's vasculature or indirectly via a transcutaneous probe. Information from the detector can then be sent to a processor which includes software for analyzing the afferent and efferent light in order to determine the level of oxygen contained in the patient's blood. More specifically, the software contains routines for analyzing the ratio of absorbances of the two emitted wavelengths and then determining blood oxygen saturation based on that ratio.

Current oximetry devices include probes that are placed on the skin or catheters that are placed in an artery such as the pulmonary artery. However both of the devices are unable to provide an indication of what the localized oxygen saturation is at a tissue site beneath the skin (other than the finger tip). Rather, they only provide an indication of what the systemic blood oxygen saturation is. Localized blood oxygen saturation for tissue sites beneath the skin can be used to diagnose a number of conditions including any number of conditions causing localized ischemia such as deep vein thrombosis, peripheral vascular occlusion, edema and cancer. What is needed is a device and method for measuring blood oxygen saturation at a localized level at a selected tissue site to facilitate diagnose of these and other diseases and conditions.

Also, current oximetric devices cannot be left in place for any extended period of time due to the requirement of having an in dwelling catheter or having a finger probe attached to the oximeter. What is also needed is an oximetric measurement device which can be left within the patient for an extended period without requiring the patient to be bedridden or otherwise tethered to an instrument.

BRIEF DESCRIPTION OF THE INVENTION

Embodiments of the invention provide an apparatus, system and method for the in vivo measurement of blood oxygen saturation. Various embodiments provide an apparatus, system, and method for measurement of localized blood oxygen saturation, using an implantable device. Many embodiments provide an apparatus for measurement of localized blood oxygen saturation which can be placed beneath the skin surface at a selected target tissue site using a syringe or other tissue penetrating device such as a trocar. In use such embodiments allow for the localized detection of underperfused and/or hypoxic tissue. Such embodiments are particularly useful for the detection of various diseases and conditions such as cancer, peripheral arterial stenosis, peripheral neuropathy, diabetes and other condition One embodiment provides an apparatus for measurement of blood oxygen saturation in a patient comprising a housing having a wall and an interior volume and an optical emitter, optical detector, controller and power source, one or more of which are positioned on or within the housing. The housing can have one or more of a size, shape and column strength to be injected through a hollow tissue penetrating device (e.g., a syringe, trocar, catheter or like device) into a target tissue site beneath the skin of the patient such as an intramuscular site by the application of a force to the housing, for example by the plunger of a syringe. At least a portion of the housing wall comprises an optically transparent material such as glass or a transparent polymer to allow light to pass in and out of the housing. The emitter is arranged and configured to emit light through the transparent portion of the housing wall and into the tissue site to measure a blood oxygen saturation within the tissue site. The light emitted from the emitter has at least one wavelength whose absorbance is related to a level of blood oxygen saturation and a second wavelength whose absorbance is substantially unaffected by the oxygenated state of blood. The emitted light will typically include a first and a second wavelength with the first wavelength in the range of about 600 to 750 nm and the second wavelength in the range of about 850 to 1000 nm. In specific embodiments, the first wavelength is about 660 nm and the second wavelength is in the range of about 900 to 950 nm. Additional numbers and ranges of wavelengths are also contemplated.

The optical detector is positioned and arranged to receive light reflected from the tissue site and detect at least the first and second wavelengths and generate a detector output signal responsive to an intensity of the detected light. The controller is positioned within the housing and is operably coupled to the detector and emitter to send signals to the emitter to emit light and receive the detector output signal. The controller can include logic for calculating a blood oxygen saturation level using the detector output signal and generating a signal encoding the blood oxygen saturation level. In particular embodiments, the controller can correspond to a microprocessor with the logic corresponding to software modules operable on the microprocessor. The power source is positioned within the housing for powering at least one of the controller, the emitter or the detector. Typically, the power source is directly coupled to at least the controller but may be coupled to other components as well including for example a recharging device such as an energy harvesting mechanism. In many embodiments, the power source comprises a miniature lithium battery known in the art such as a lithium ion battery.

In various embodiments of the invention, the apparatus may include a magnetic hook which may comprise a magnet or a non-magnetic ferrous structure positioned on or within the housing to allow the apparatus to be removed from the tissue site or otherwise manipulated beneath the skin to facilitate removal using a removal tool containing a magnet or magnetized portion. The force of magnetic attraction between the hook and the removal tool magnetic portion being sufficient to pull the apparatus from the tissue site to the skin surface (i.e., beneath the skin surface) so that the apparatus can be easily removed with a very shallow incision in the skin. The removal tool may comprise a magnet itself or a finger grippable shaft attached to the magnet, allowing a physician to have finer control over the second magnet. In a particular embodiment, the magnet on the removal tool may comprise an adjustable electromagnet allowing the physician to adjust the amount of magnetic force used to remove the apparatus. In a related embodiment, the magnetic hook may comprise a ferrous-based suture or wire, herein, "a pull wire", attached to the exterior surface of the housing which allows the physician to first pull the wire or suture to the skin surface using the removal tool and then pull the apparatus out to the tissue using the pull wire. In some embodiments, the pull wire can include a loop on its non-attached end to facilitate grasping of the wire once it is brought near the skin surface. The benefits of using the pull wire include one or more of the following: i) less magnetic force is required to remove the pull wire then that required to remove the whole housing allowing use of a less powerful second magnet; and ii) the physician can more easily and controllably remove the entire apparatus using the pull wire then removal by magnetic attraction alone which should reduce both tissue trauma and pain. In some embodiments, a combination of an internal magnetic hook and an external ferrous-based pull wire can be used to further facilitate atraumatic removal of the apparatus. Removal of the apparatus can also be facilitated by fabricating portions of the housing from radio-opaque, echogenic or other materials visible under a selected medical imaging modality and/or attaching to the housing one or more medical imaging markers such as radio-opaque and/or echogenic markers.

In various embodiments of the invention, all or a portion of the apparatus housing can be fabricated from shape memory materials such as nickel titanium alloys allowing the apparatus to be placed at the selected tissue sit; with the apparatus having a first size and shape and then upon exposure to body temperature within the tissue site, the apparatus expands to a second size and shape. In particular embodiments, the housing can be configured expand so as to anchor the housing at the tissue site. For example, in one or more embodiments, the housing can be fabricated from shape memory materials configured to expand to an hour glass or other like shape with the ends of the housing flaring out to hold the apparatus in place at the tissue site. In use, such embodiments allow the housing to have a smaller size to facilitate placement at the selected tissue site and then to expand to the larger size and/or shape to anchor the apparatus at the tissue site so as minimize movement of the apparatus once placed at the site. In related embodiments, all or a portion of the housing can be fabricated from shape memory materials having pseudo-elastic properties such as nickel titanium alloys (an example including NITINOL) configured to undergo a change in stiffness upon exposure to body temperature. Typically, this change will entail going from a more rigid state to a more flexible state (though the reverse is also contemplated). Such embodiments allow the apparatus to have a more rigid quality to facilitate insertion at the tissue site and then once placed, become more flexible to allow the housing to bend and flex with movement of the body including movement of tissue at the tissue site. In one embodiment, the center portion of the housing can be configured from a shape memory material which becomes elastic at body temperature allowing the center portion of the housing to bend and flex with movement of body tissue. Such embodiments of the housing having pseudo elastic properties also facilitate removal of the apparatus from the patient's body and reduce trauma since the housing can bend when grasp by a forceps or attracted by a magnetic removal tool allowing the housing to be bent up toward the skin surface or otherwise manipulated while imparting less force to surrounding tissue.

In other aspects of the invention, embodiments of the measurement apparatus can be adapted for numerous applications in the medical field including diagnostic and prognostic applications. Such applications can include, for example, tumor monitoring including monitoring a tumor for the efficacy of chemotherapy by using the oxygenated state of tissue in and around the tumor as an indication of the size and viability of the tumor. In use, such tumor monitoring applications allow a course of chemotherapy to be titrated responsive to the effects on the tumor of the chemotherapy. This improves both treatment efficacy and long term patient tolerance. For example, the dose of a particular chemotherapeutic compound with side effects such as nausea could be reduced upon determination that the tumor is shrinking, improving patient tolerance.

In another application, an embodiment of the oxygen saturation measurement apparatus can be adapted for monitoring the health and/or viability of an organ transplant by measuring the oxygenated state of tissue in and around the organ. Change such as decreases in oxygen saturation including rapid decreases being indicative of tissue rejection or the onset of tissue rejection. This in turn, allows time for rapid medical intervention to save the transplanted organ. In another application, embodiments of the apparatus can be used to monitor for oxygen saturation in the extremities of diabetic patients (who are prone to develop neuropathy in their extremities) allowing for medical intervention before the development of neuropathy. In still other applications, embodiments of the invention can be used for monitoring patients who have chronic obstructive pulmonary disease (COPD) or other respiratory disorders allowing for early diagnosis and treatment of an adverse respiratory state in such patients. Related embodiments can be use to monitor oxygen saturation levels of patients having congestive heart failure (CHF) again allowing for early diagnosis and treatment of various related conditions, e.g., pulmonary edema, before they become life threatening. In still other applications, embodiments of the invention can be used to monitor the progress of wound healing at a selected tissue site allowing for the early detection and treatment of acute conditions such as infection as well as monitoring the longer term progress of the wound healing process. Infection may be characterized by either a rise or fall in tissue oxygen saturation at the site depending upon the type of bacteria. For example, changes (e.g., lower) in the levels of oxygenation may be utilized as biomarkers/predictors of slower or other atypical healing requiring medical intervention (e.g., through the administration of one or more drugs, such as growth hormone, erythropoietin or other like compounds). Such predictions can be achieved by developing correlations between the time course of the healing process and levels of tissue oxygen saturation at site including rates of change of oxygen saturation. Still other related applications are also contemplated by various embodiments of the invention as will be known to those skilled in the medical diagnostic and other related arts. The features and attributes of the oxygen saturation measurement apparatus can be customized for each application, with such features including one or more of the size, shape, surface coatings, emitted and detector configuration and the wavelength, intensity and duty cycle of the emitted wavelength and other like factors. For example, the wavelength, intensity and duty cycle of the emitted light may be fine tuned for increased sensitivity to detect lower levels of blood oxygen saturation found in one or more of deep vein thrombosis, infected or tumerous tissue.

In yet another aspect of the invention, embodiments of the invention provide a kit for measuring blood oxygen saturation comprising embodiments of the oxygen saturation measurement apparatus described herein and instructions for using the apparatus alone and/or in conjunction with a monitoring device including a portable monitoring device which allows for the monitoring of signals transmitted from the apparatus. Such signals can include information on measured oxygen saturation. The instructions may either be in printed form or in electronic media such as a ROM or other memory resources integral to the monitoring device or a CDROM. The instructions may include specific instruction for establishing a communications link between the apparatus and the portable monitoring device which can be a custom device or an off the shelf cell phone or PDA like device. Further, specific embodiments of the instructions can describe how to couple and use the apparatus with one or more of an APPLE IPHONE, IPAD, IPOD or like portable device running one or more software applications for deep vein thrombosis detection.

Embodiments of the instructions can also include specific instructions for doing one or more of the following: calibrating the apparatus, taking baseline measurements, instructions for how to use the apparatus to detect various conditions such as deep vein thrombosis; and instructions for reading and/or interpreting a display of the portable monitoring device to determine the presence of a deep vein thrombosis. These and other features and embodiments of the invention are described in detail in the body of specification.

BRIEF DESCRIPTION OF THE DRAWINGS

FIGS. 4d-4f illustrate an embodiment of an oxymetric measurement apparatus having a biodegradable tissue penetrating attachment.

DETAILED DESCRIPTION OF THE INVENTION

Referring now to FIGS. 1-9, an embodiment of an apparatus 10, for measurement of blood oxygen saturation in a patient P comprises a housing 20 having a wall 25 (having an exterior and interior surface 21 and 22) interior volume 26; and an optical emitter 30, optical detector 40, controller 50, electronic devices 60 and power source 70 (also referred to herein as power supply 70). One or more of these components may be positioned within or on the housing 20. Additionally, one or more of these or other electrical components of apparatus 10 may be positioned on or otherwise electrically coupled to a printed circuit board 15 (or like component) to facilitate ease of manufacturing and/or achieve a selected form factor for insertion and fit within the interior volume 26 of housing 20. In particular embodiments, printed circuit board 15 can be configured to allow for connection of electrical components of apparatus 10 on both sides 16 and 17 of the board to allow for space savings within housing 20. For example in one embodiment, an integrated circuit 53 corresponding to controller 50 or an ASIC 55 may be placed on a bottom side 17 of board 15 while other components such as emitter 30, detector 40 and devices 60 are placed on the top side 16. Devices 60 may include for example, resistors capacitors, inductors and may be arranged to form one or more circuits 61, for example an LC circuit, or RC circuit 61.

Housing 20 has a size, shape and column strength to be injected or otherwise advanced through a hollow tissue penetrating device 200 such as a syringe 201 into a target tissue site TS beneath the skin S of the patient P, (for example, an intra-muscular site within muscle M) by the application of force to the housing as is shown in the embodiments of FIGS. 1 and 4a-4c. Typically, the force will be applied to a proximal portion 23p (the end which enters tissue last) of housing 20, for example by the plunger 202 of syringe 201. In various embodiments, use of other tissue penetrating devices 200 is also contemplated for advancement of apparatus 10 into tissue including one or more of a trocar, catheter or endoscope. In particular embodiments, housing 10 can be configured to be inserted directly into tissue without use of a tissue penetration device 200 by the application of force onto a proximal 23p or other portion of housing 20.

In particular embodiments, housing 20 can have a cylindrical like shape with its distal end 23 (the end which enters tissue first) having a tapered shape or other tissue penetrating shape to facilitate tissue penetration. In these and related embodiments, housing 20 can comprise a body 27 and a cap 28 which is hermetically sealed to body 27 using an adhesive or other sealing method known in the art (e.g., ultrasound welding, etc.).

Figure 1:
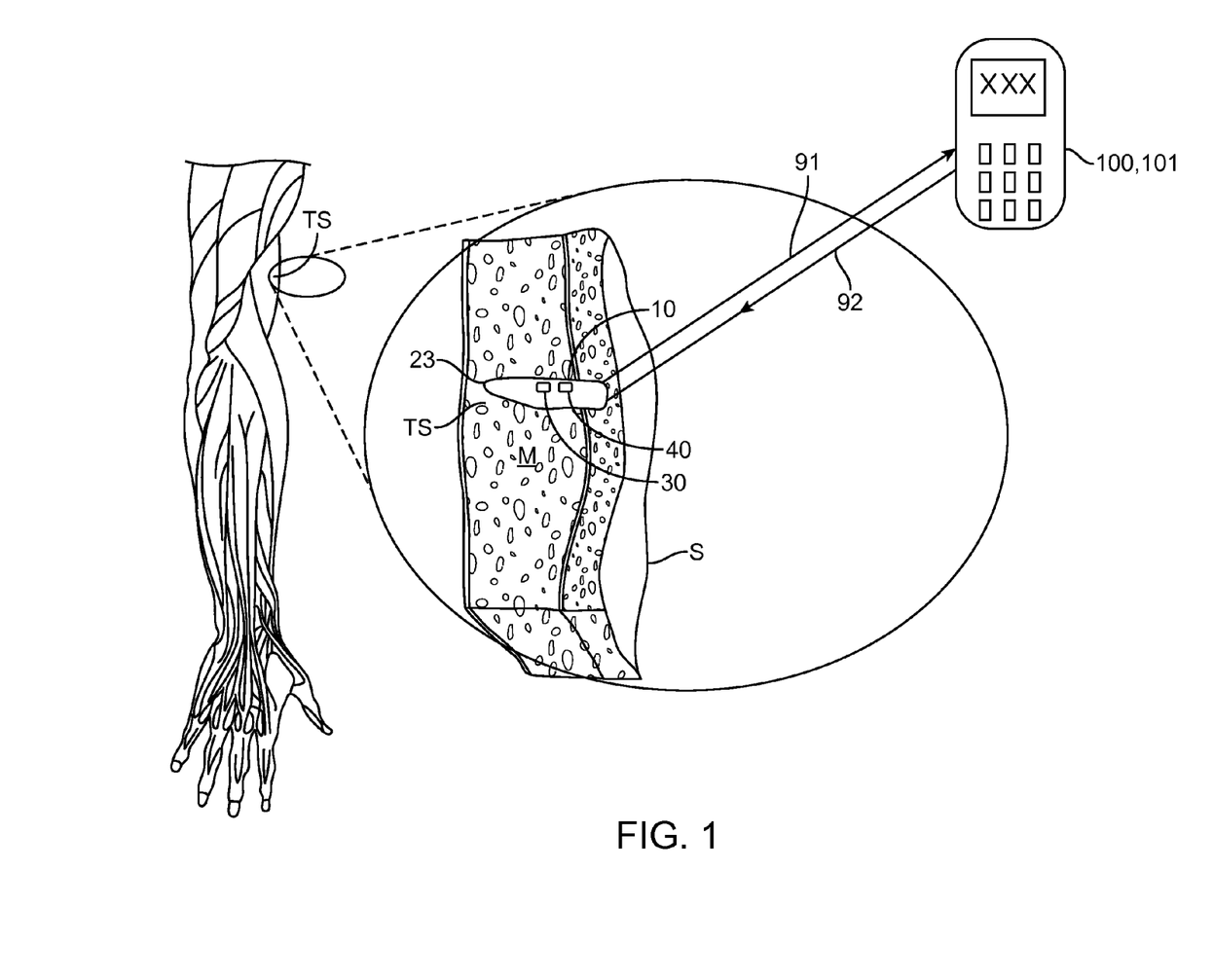
FIG. 1 is a perspective view illustrating an embodiment of an implantable oxymetric measurement apparatus positioned at target tissue site within a patient.
Figure 2:
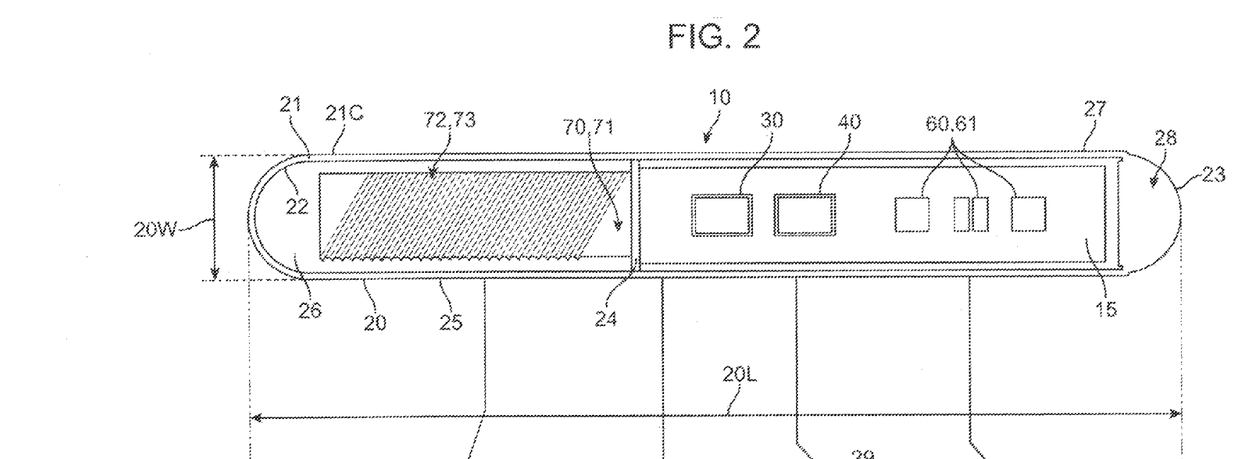
FIG. 2 is a top view illustrating an embodiment of an implantable oxymetric measurement apparatus.
Figure 3A:
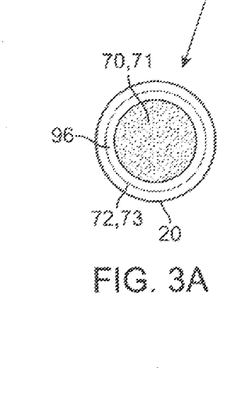
FIGS. 3a-3d are cross sectional orthogonal views of the embodiment of FIG. 2, illustrating the arrangement and positioning of components of the implantable oxymetric measurement apparatus at various locations over the length of the apparatus.
Figures 3B, 3C:
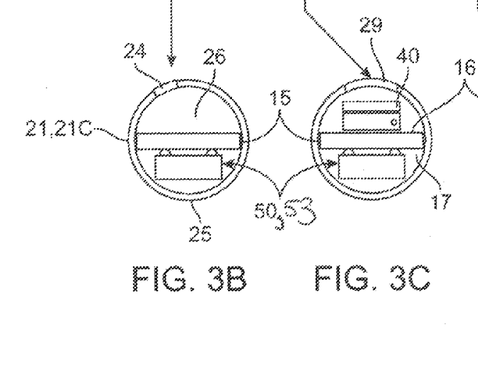
Figure 3D:
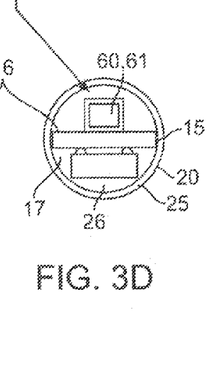
Figure 4A:
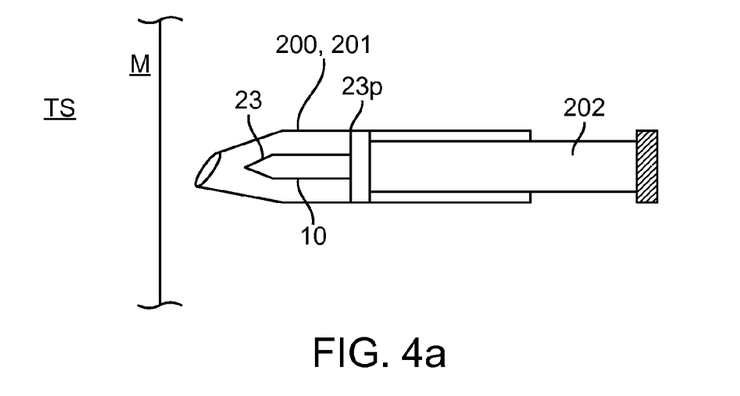
FIGS. 4a-4c illustrate placement of an embodiment of an oxymetric measurement apparatus at a target tissue site within a patient using a tissue penetrating device such as a syringe.
Figure 4B:
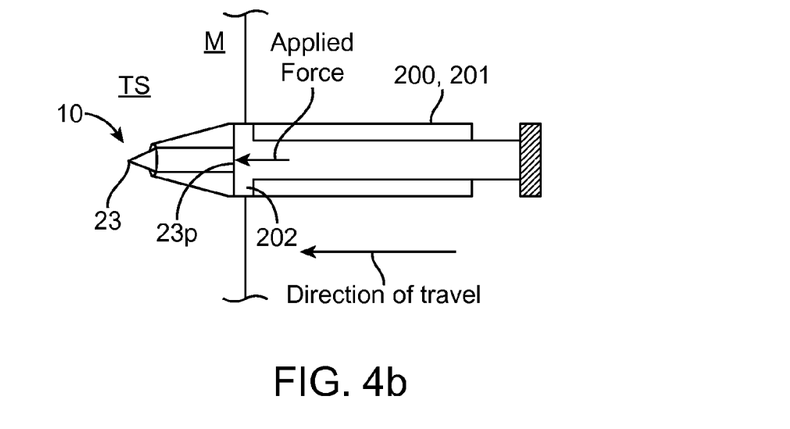
Figure 4C:
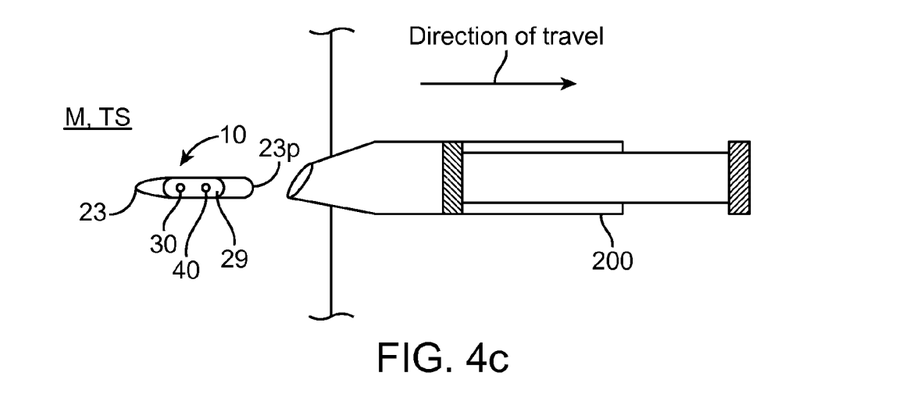
Figure 4D:
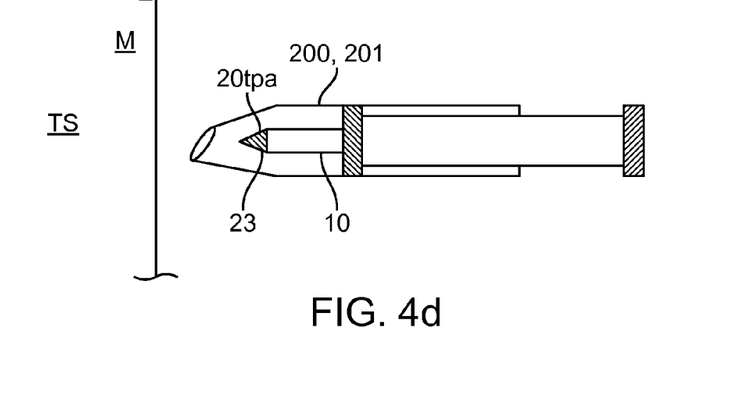
FIGS. 4d and 4e illustrate insertion of the apparatus into tissue and FIG. 4f illustrates the shape of the apparatus after the attachment has degraded to yield an atraumatic shape for the attachment housing.
Figure 4E:
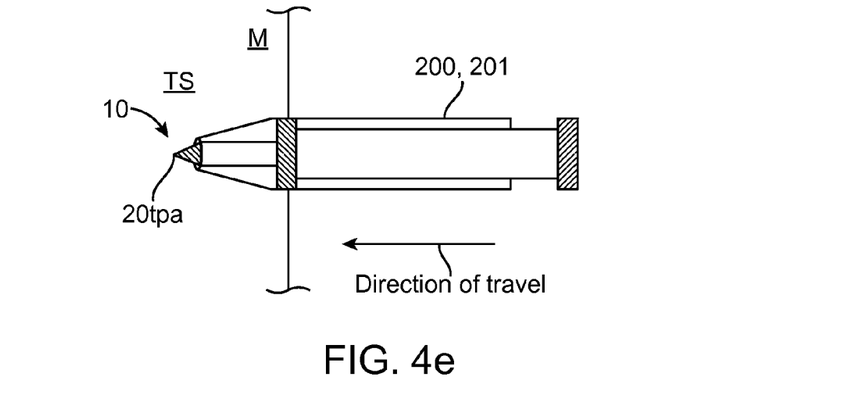
Figure 4F:
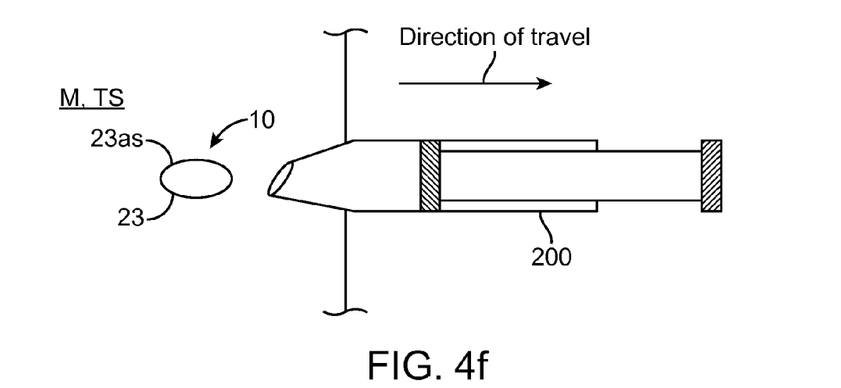

In particular embodiments shown in FIGS. 4d-4f, a tissue penetrating attachment 20tpa can be attached to the distal end 23 of housing 20. Tissue penetrating attachment 20tpa can have a pointed or other tissue penetrating shape and is desirably fabricated from a biodegradable material such as maltose, sucrose, PGLA (Poly Lactic-co-Glycolic Acid), or other like material which degrades soon (e.g., 1 to 2 minutes to an hour) after apparatus 10 is positioned at tissue site TS. Use of the biodegradable material for the tissue penetrating attachment 20tpa allows apparatus 10 to be readily inserted into tissue (alone or with use of a syringe) and then after insertion, have the tissue penetrating attachment 20tpa degrade to yield a smooth atraumatic shape 23 as for the distal end of 23 of housing 20 so as to provide for the long term biocompatibility of apparatus 10 at a tissue site TS. In use, this allows for apparatus 10 to be readily tissue insertable on the one hand and on the other, provide for the long term measurement of blood oxygen saturation levels.

The length 201 of housing 20 can be in the range of about 4 to 10 cms, with specific embodiments of 5, 6, 7, 8 and 9 cms, while the width 20w can be in the range of about 0.5 to 2 mm, with specific embodiments of 1, 1.25 and 1.5 mms. Length 201 and width 20w are desirably selected to allow sufficient interior volume for placement of emitter 30, detector 40 controller 50, devices 60 and power source 70 within housing 20. In particular embodiments, length 201 and width 20w can be selected to allow for a linear arrangement of emitter 30, detector 40, controller 50, devices 60 and power source 70.

In various embodiments, the column strength of housing 20 can range from about 0.1 lbs (force) to 5 lbs, with specific embodiments of 0.2, 0.25, 0.3, 0.5, 0.75, 0.8, 1.0, 2.0, 2.5, 3 and 4 lbs force. The column strength of housing 20 can be achieved through one more of the selection of materials for the housing as well as the thickness of wall 25. Suitable materials for housing 20 in this regard include various biocompatible polymers known in the art including various rigid biocompatible polymers such as PET, HDPE, polymethylmethacrylate (PMMA) and like materials. The column strength of one or more of these materials, such as HDPE may be increased by exposure to electron beam to radiation to achieve cross linking of polymer chains as is known in the catheter arts. Also in various embodiments, all or portions of the housing can be fabricated from radio-opaque and/or echogenic materials to achieve visualization of the housing under fluoroscopy, ultrasound or other medical imaging modality. In related embodiments, housing 20 can include one or more medical imaging markers 24 such as radio-opaque, echogenic, or other marker fabricated from a material visible under a selected medical imaging modality.

In various embodiments, all or a portion of the housing 20 can include a coating 21c such as silicone, PTFE or polyurethane to achieve one or more of the following: i) impart a greater degree of biocompatibility to housing 20; ii) reduce the amount of cellular and other bio-adhesion to exterior surface 21; and iii) provide a lubricous surface facilitating placement of the housing a selected tissue site. In an alternative or additional embodiment, coating 21c can also include a drug eluting coating such as paclitaxel or various steroids for reducing cellular adhesion to exterior surface 21.

At least a portion of the housing wall 25 comprises an optically transparent material such as glass or an optically transparent polymer to allow light to pass in and out of the housing. Suitable optically transparent materials include glass, PMMA, polydimethylsiloxane and hydrogels including high stiffness hydrogels. In some embodiments, the entire housing 20 is fabricated from an optically transparent material. In others, the housing includes an optical window 29 (fabricated from optically transparent material) under which, the emitter 30 and detector 40 are positioned. Emitter 30 is arranged and configured to emit light through optical window 29 and into tissue site to measure a blood oxygen saturation within the tissue site. One or both of the emitter 30 and detector 40 can be positioned flush against the inside surface 22 of wall 25 or may be recessed a selected amount and may be positioned at a selectable angle with respect to the plane of wall 25 so as to achieve a desired angle of incidence and reflectance.

Figure 5:
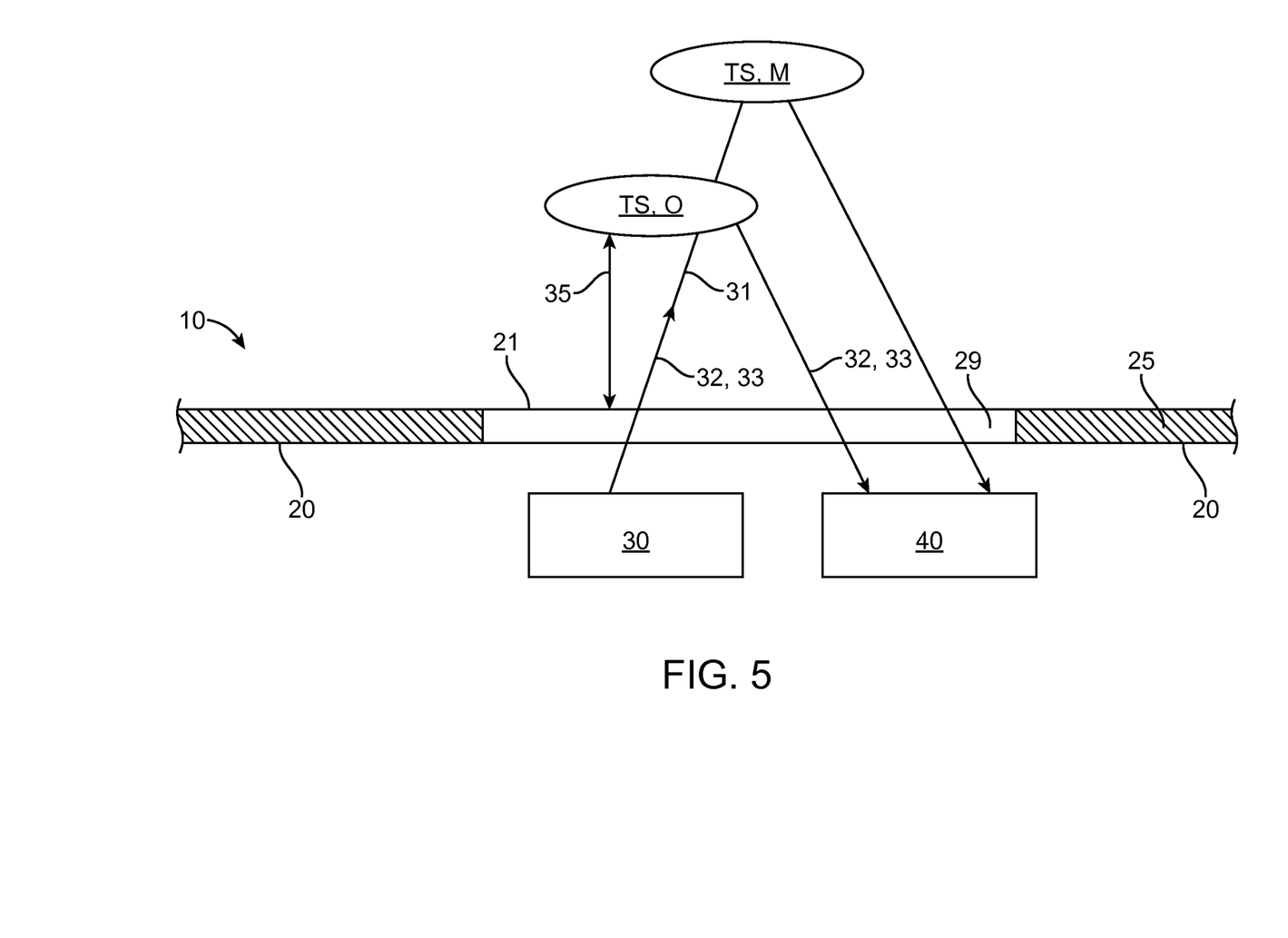
FIG. 5 is a lateral view illustrating the position and operation of an embodiment of an emitter and detector used in one or more embodiments of the invention.

According to one or more embodiments, emitter 30 can comprise a single or multiple LEDS. It may also include various single or multi-wavelength LEDS known in the art. The light emitted 31 from emitter 30 has at least one wavelength 32 whose absorbance is related to a level of blood oxygen saturation and a second wavelength 33 whose absorbance is substantially unaffected by the oxygenated state of blood. First wavelength 32 can be in the range of about 600 to 750 nm and the second wavelength 33 in the range of about 850 to 1000 nm. In specific embodiments, the first wavelength is about 660 nm and the second wavelength is in the range of about 900 to 950 nm. Additional values and ranges of wavelengths are also contemplated. Both first and second wavelengths 32 and 33, as well their intensity, can be adjusted depending upon the selected tissue site TS, for example, organ O versus muscle M, with adjustments made for the optical properties of a specific tissue site (e.g., absorbance of specific wavelengths). In particular embodiments, the intensity of one or both of wavelengths 32 and 33 can be adjusted to penetrate a selected distance 35 into the tissue at the target tissue site, for example penetrating up to about 0.5 cm, 1 cm, up to about 2 cm and up to about 3 cms, with larger and smaller depths contemplated. The penetration depth 35 and corresponding intensity can be adjusted depending upon the application, for example, tumor monitoring, wound healing monitoring, CHF monitoring or COPD monitoring. Additionally, the intensity of wavelengths 32 and 33 can be adjusted over time can be adjusted (typically increased) to compensate for the buildup of adhered protein, cells and other tissue on housing exterior surface 21 which may reduce the transmission of light through optical window 29 and/or wall 25.

The optical detector 40 is positioned and arranged to receive light reflected from the tissue site TS and detect at least one wavelength and generate a detector output signal responsive to an intensity of the detected light. In various embodiments, detector 40 can comprise one or more of a photodiode, photo transistor, photomultiplier, CCD or other like device. Also, desirably detector 40 is configured to detect light at multiple wavelengths (e.g., two, three, four, etc). Detector 40 can be positioned in the interior surface 22 of housing wall 25 or it may be recessed.

Figure 6:
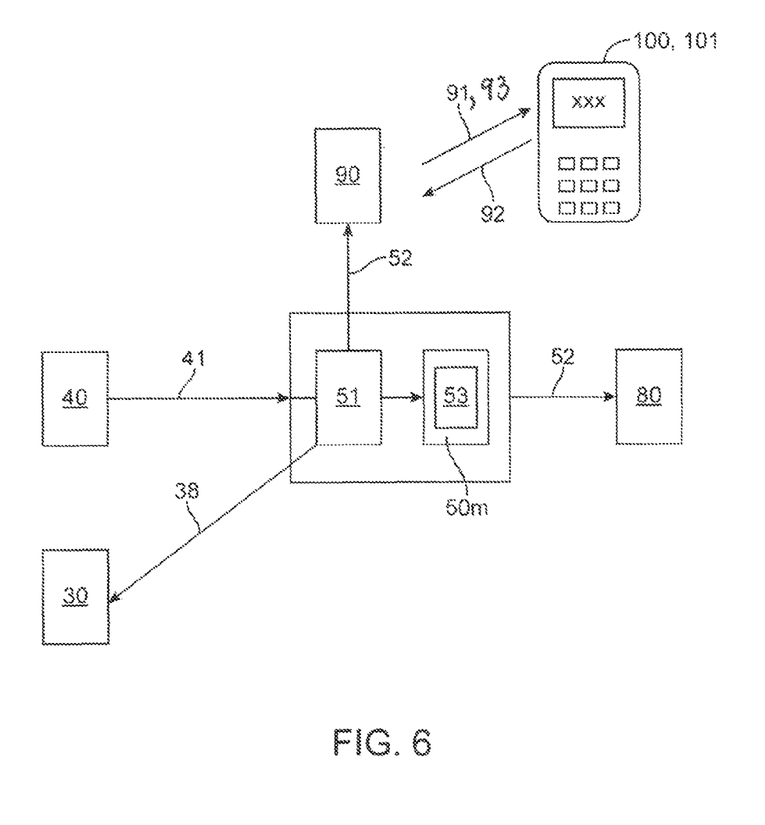
FIG. 6 is a block diagram illustrating an embodiment of a controller having one or more software modules for control of one or more operations of embodiments of the oximetric measurement apparatus.

Controller 50 is operably coupled to one or more components of apparatus 10 so as to control various components and/or operations of the apparatus. This may be accomplished by coupling the controller to printed circuit board 15 on which one or more other electric components are coupled. In various embodiments, controller 50 may correspond to one or more of analog control circuitry, a state device, a microprocessor or software operable on a microprocessor or other like device. In particular embodiments, controller 50 is coupled to emitter 30 and detector 40 to send signals 38 to the emitter 30 to emit light and receive signals 41 from the detector 40 corresponding to intensity of detected light. Controller 50 may include logic such as software, firmware, hardware or combinations thereof for controlling one or more operations of apparatus 10, such as emission of light by emitter 30, power management, power coupling, calculation of blood oxygen levels and signaling information on such levels to an external device. Controller 50 may also be incorporated into an application specific integrated circuit or ASIC 55 which may also include other components of apparatus 10 such as detector 30, emitter 40, devices 60, power source 70, memory device 80 and an RF or other communication device 90. As described above controller 50 may be coupled to a circuit board 15 to allow coupling of controller 50 to these and other components.

Controller 50 may also be coupled to a memory device 80, which may correspond to ROM, RAM, DRAM or other memory device known in the art. Memory device 80 may include one or more software modules 51 for controlling one or more operations of controller 50 and apparatus 10. Modules 51 can be configured to be uploaded to controller 50 for example by programming resident within controller 50. Memory device 80 may also be configured to be reprogrammed, for example by means of communication device 90 to allow for downloading of different programs for control and operation of apparatus 10.

Figure 7:
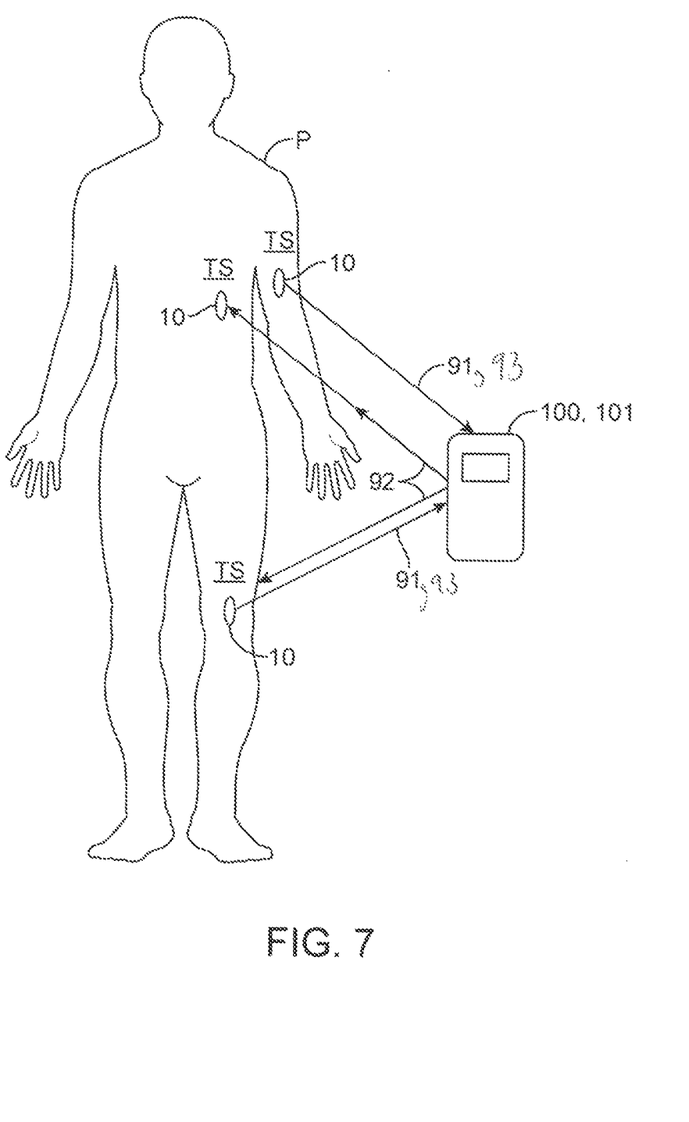
FIG. 7 illustrates use of a monitoring device and one or more oximetric measurement apparati to monitor the oxygen saturation of a patient.

In particular embodiments, controller 50 corresponds to a microprocessor and includes one or more software modules 51 for calculating blood oxygen saturation or a related parameter using the detector output signal 41 and generating an output signal 52 corresponding to that saturation level. Modules 51 may also be configured to perform one or more of the following operations: i) store output signal 52 as a stored value 53 in memory 50m of controller 50 or a separate memory device 80; ii) send output signal 52 to an RF communication device 90 for sending an RF signal 91 (corresponding to signal 52) to an external device 100; iii) direct memory device 80 to send a plurality of signals 52 (corresponding to a plurality of stored values 53) to communication device 90 for wireless communication with an external device 100 (e.g., either in continuous or a burst mode, either of which can be in response to a signal 92 from device 100 or a condition module 51 such as an oxygen saturation being below a threshold); and iv) initiate one or more oxygen saturation measurements by sending of signals 38 to emitter 30 either at selected time intervals or in response to an input such as a signal 92 from external device 100. For embodiments of apparatus 10 including a communication device 90, module 51 can be programmed to transmit signals 52, 91 continuously, at set time intervals or in response to one or more conditions being met such as oxygen saturation falling below a set threshold (e.g., 95, 90% etc.). The later case can be tailored for monitoring bedridden patients including critical care patients with the specific oxygen threshold dictated by the particular patient and their condition (e.g., peripheral claudication). In use, these and related embodiments eliminate the need to have critical care and other bedridden patients tethered to an oximeter (either via transcutaneous probe or a pulmonary arterial catheter). Also, multiple apparati 10 can be placed at a number of locations in the patient's body such as in one or more of their extremities in order to get a broader picture of perfusion and tissue oxygenation throughout the patient's body. In particular embodiments, apparatus 10 can be placed in each extremity (e.g. arms and legs) so that the medical care giver can ascertain if uniform perfusion is occurring in these locations, and if not, be able to compare perfusion/oxygenation in one limb with another, for example leg vs. arm or arm vs. arm. In a related or alternative embodiment at least a first and second apparatus 10 can be placed at two target tissue sites TS with blood oxygen measurement at the first site being compared to the second site. This can allow for determining if one site is hypoxic/underperfused compared to the second site as well as if both sites are hypoxic/underperfused to allow for a more comprehensive determination of one or more of deep vein thrombosis, transplant tissue viability/health, or tumor location or state. In another related embodiment, multiple apparati 10 can be placed at the same or different tissue sites in order to develop a map of blood oxygen saturation for a given tissue site TS or multiple tissue sites.

Power source 70 is configured to power one or more components of apparatus 10. In many embodiments, power source 70 is configured to power at least one of emitter 30, detector 40, controller 50, electronic devices 60 and communication device 90. Typically, the power source is directly coupled to at least the controller 50 but may be coupled to other components as well including for example, a recharging device such as an energy harvesting mechanism. Typically, power source 70 is positioned within housing 20 but also may be disposed on the housing exterior. In many embodiments, the power source 70 comprises a miniature battery 71 such as a lithium or lithium ion battery which can include rechargeable batteries. Desirably, the battery 71 has a form factor such as a cylindrical form factor which corresponds to the shape of housing interior volume 26. In one alternative embodiment, power source 70 may also correspond to a super capacitor.

In various embodiments power source 70 may also include a conductive coil 72 arranged and configured for recharging various embodiments of a rechargeable power source 70 (e.g., a rechargeable battery, super capacitor, etc.) source via conductive coupling methods known in the art. In particular embodiments, coil 72 can be wrapped around a battery 71 in order to conserve space inside housing 20. Coil 72 may also be configured as an antenna 96 for communication device 90. In related embodiments, coil 72 can also be configured as a magnetic hook 75 for removing apparatus 10 from tissue site TS using a magnetic removal tool 210 as is described below. In such embodiments, coil 72 is fabricated from ferrous material and may be magnetized or configured as an electro-magnet powered by a battery power source 70.

Communication device 90 can comprise one or more of a radio frequency (RF), optical or acoustical based communication device. In preferred embodiments, communication device 90 can comprise an RF chip configured to send and receive signals at one or more frequencies or ranges of frequencies. In various embodiments, the range of frequencies can be in a range of about 400 MHz to 6 GHz with a specific embodiment of about 402 to 405 MHz so as to correspond to the Medical Implant Communications Services (MICS) standard established by the Federal Communications Commission (FCC). Communication device 90 can be configured to wirelessly communicate with an external device 100 (e.g. a portable communication device 101 such as a cell phone) described below so as to send signals 91 encoding data on blood oxygen saturations generated by apparatus 10. Signals 91 may also encode information such as the charge state/remaining life of a battery power supply 70, the condition of emitter 30 and detector 40, and the degree of transparency of optical window 29 so as to assess the amount of cellular or proteneous matter coating the window. Communication device 90 can also be used to reprogram controller 50 and/or memory device 80.

Various embodiments of the invention also provide an external device 100 for monitoring signals 91. External device 100 may also be configured for two-way communication with device 10 including receiving signals 91 and sending signals 92. External device 100 can comprise a portable communication device 101 for wireless communication with apparatus 10. In various embodiments, portable device 101 may correspond to a cell phone, a PDA, notepad or other like device. External device 100 may also be configured to be inductively coupled to conductive coil 72 so as to recharge embodiments of a rechargeable power supply 70. In various embodiments external device 100 may be configured to monitor and communicate with multiple apparati 10. In these and related embodiments, each apparatus 10 can be configured to have a distinct RF communication frequency and/or an identifying signal 93. External device 100 may be configured to simultaneously monitor apparati 10, or to do so serially for example, by cycling through a range of selected frequencies corresponding to those used by individual apparatus 10.

Figure 8A:
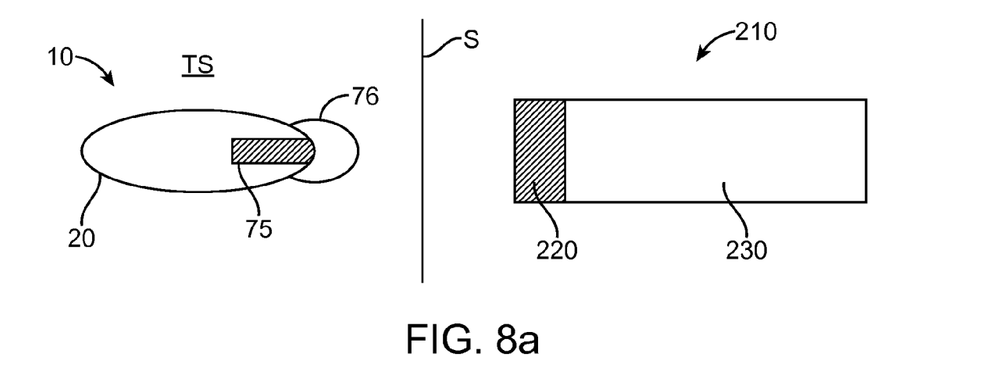
FIGS. 8a-8c illustrates embodiments of an oximetric measurement apparatus having a magnetic hook and use of a magnetic removal tool to remove the measurement apparatus by the magnetic hook.
Figure 8B:
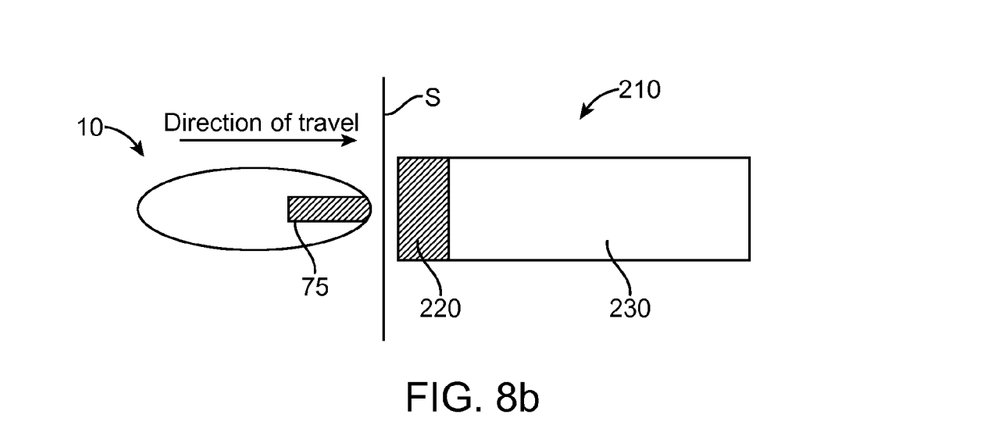
Figure 8C:
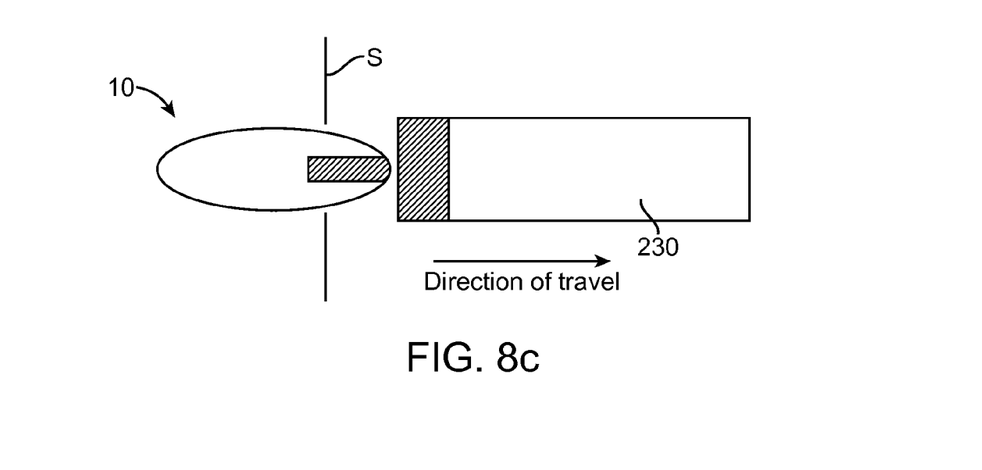

In another aspect of the invention, embodiments of the invention provide a means for removing apparatus 10 from a tissue site TS using magnetic force. Referring now to FIGS. 8a-8sc, in various embodiments, apparatus 10 may include a magnetic hook 75 positioned within or on housing 20 to allow the apparatus to be removed from the tissue site TS, for example by a removal tool 210 (or other removal means 210) including a magnet 220. Magnetic hook 75 can comprise magnetized material or can comprise non-magnetic ferrous material. In some embodiments, magnetic hook 75 may comprise coil 72 as discussed above. The force of magnetic attraction between magnetic hook 75 and magnetic 220 is configured to be sufficient to pull the apparatus 10 from the tissue site to the skin surface (i.e., beneath the skin surface) so that apparatus 10 can be readily removed from tissue site TS with a very shallow incision in the skin (or in some cases, no incision at all). The removal tool 210 will typically include a finger grippable shaft 230 or grippable means 230 to which magnet 220 is attached, allowing a physician to have finer control over movement of second magnet 220. In alternative embodiments, removal tool 210 may comprise magnet 220 itself without a shaft. Magnet 220 can also be an adjustable electromagnet allowing the physician to adjust the amount of magnetic force used to remove the apparatus. In alternative embodiments, magnetic hook 75 may comprise a ferrous based suture or wire 76, herein a "pull wire" 76, attached to the exterior surface of housing 20 which allows the physician to first pull the wire or suture to the skin surface using removal tool 210 and then pull the apparatus out to the tissue surface using the pull wire 76. In some embodiments, the pull wire 76 can include a loop on its non-attached end to facilitate grasping of the wire once it is brought near the skin surface. The benefits of using pull wire 76 include one or more of the following: i) less magnetic force is required to remove the pull wire to skin surface then the whole housing 20 allowing use of a less powerful magnet 220; and ii) the physician can more easily and controllably remove the entire apparatus 10 using the pull wire 76 then by magnetic attraction alone which should reduce both tissue trauma and pain. In some embodiments, a combination of an internal magnetic hook 75 and a ferrous-based pull wire 76 can be used to further facilitate atraumatic removal of the apparatus. Removal of the apparatus can also be facilitated by fabricating portions of the housing 20 from radio-opaque, echogenic or other materials visible under a selected medical imaging modality and/or attaching to the housing one or more medical imaging markers such as radio-opaque and/or echogenic markers.

Figure 9:
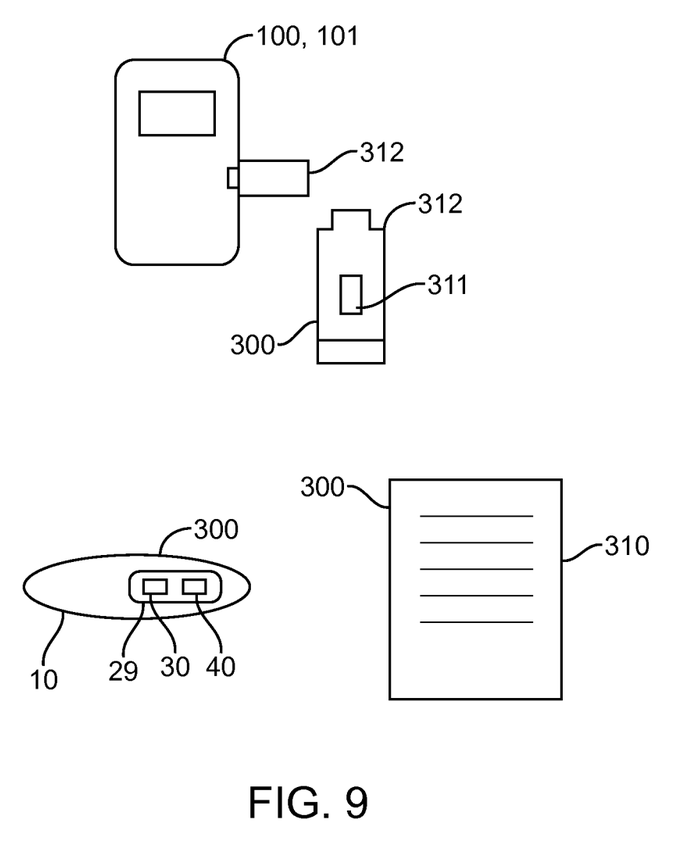
FIG. 9 is a perspective view illustrating an embodiment of an oximetric measurement kit including an oximetric measurement apparatus and instructions for using the oximetric measurement apparatus.

Referring now to FIG. 9, in yet another aspect of the invention, embodiments of the invention provide a kit 300 for measuring blood oxygen saturation comprising embodiments of the oxygen saturation measurement apparatus 10 described herein and instructions 310 for using apparatus 10. Instructions 310 may include instructions and other information for using the apparatus alone and/or in conjunction with portable monitoring device 101 described herein which allows a medical care giver to monitor signals 91 transmitted from apparatus 10 which include information on measured oxygen saturation or other biometric data. The instructions 310 may either be in printed form or an electronically stored form 311 stored in electronic media 312 including for example, the internet, CD-ROM, or a memory device such as a flash drive which is supplied with kit 300. For embodiments using electronically stored form of instructions 311, the instructions can be downloaded onto communication device 101 using the internet or uploaded from a flash drive or CD-ROM or other electronic storage media. The instructions 310 may include specific instruction for establishing a communications link between the apparatus 10 and the portable monitoring device 101 which can be a custom device or an off the shelf device such as a cell phone, notepad (e.g., an APPLE IPAD) or PDA like device. Further, specific embodiments of instructions 300 can describe how to couple and use the apparatus 10 with one or more of an APPLE IPHONE, IPAD, IPOD or like portable device running one or more software applications for deep vein thrombosis detection.

Further in various embodiments, instructions 310 may include specific instructions for performing one or more of the following: i) calibrating the apparatus, ii) taking baseline oxygen saturation measurements, iii) how to use the apparatus to detect various conditions such as deep vein thrombosis; iv) how to read and/or interpret a display of the portable monitoring device to determine the presence of a deep vein thrombosis or other condition, for example instruction for reading/interpretting a graph, numerical value, symbol or message on the display.

Conclusion

The foregoing description of various embodiments of the invention has been presented for purposes of illustration and description. It is not intended to limit the invention to the precise forms disclosed. Many modifications, variations and refinements will be apparent to practitioners skilled in the art. For example, various embodiments of the apparatus can be adapted for measurement of other blood gases and any number of bio-analytes (e.g., blood sugar, glycolated hemoglobin) which may correspond to biomarkers of various conditions (e.g., hypoglycemia, hyperglycemia, etc.). Further various embodiments may also be configured for one or more ventinary applications, such as for example use in a canine, feline, equine, bovine or other farm animal. Such application can include use of one or more wireless transmission devices such an RF transmitter or wireless transmission means so that that condition of an animal or animals can be monitored remotely.

Elements, characteristics, or acts from one embodiment can be readily recombined or substituted with one or more elements, characteristics or acts from other embodiments to form numerous additional embodiments within the scope of the invention. Moreover, elements that are shown or described as being combined with other elements, can, in various embodiments, exist as standalone elements. Hence, the scope of the present invention is not limited to the specifics of the described embodiments, but is instead limited solely by the appended claims.

What is claimed is:

1. An implantable apparatus for measuring blood oxygen saturation levels in a patient, the apparatus comprising:
   a housing having a wall and an interior volume, at least a portion of the housing wall comprising an optically transparent material, the housing having a size, shape and column strength to be injected through and released from a hollow tissue penetrating device into an intramuscular target tissue site beneath a skin of the patient by the application of a force on a proximal end of the housing;
   an optical emitter positioned within the housing, the emitter arranged and configured to emit light through the housing wall and into the tissue site to measure a blood oxygen saturation within the tissue site, the emitted light having at least one wavelength whose absorbance is related to a level of blood oxygen saturation;
   an optical detector positioned within the housing and arranged to receive light reflected from the tissue site, the optical detector configured to detect light at the at least one wavelength and generate a detector output signal responsive to an intensity of the detected light;
   a processor positioned within the housing and operably coupled to the detector and emitter to send signals to the emitter to emit light and receive the detector output signal, the processor including logic for calculating a blood oxygen saturation level using the detector output signal and generating a signal encoding the blood oxygen saturation level and logic to adjust at least of an intensity or wavelength of the emitted light to penetrate a selectable depth into tissue at the target site; and
   a power source positioned within the housing for powering at least one of the processor, the emitter or the detector, the power source coupled to at least the processor.

2. The apparatus of claim 1, wherein the housing has a substantially tubular shape.

3. The apparatus of claim 1, wherein the tissue penetrating device comprises a syringe.

4. The apparatus of claim 3, wherein the syringe includes a needle and the housing is configured to be injected into the tissue site through the needle.

5. The apparatus of claim 1, wherein the optically transparent material comprises glass or an optically transparent polymer.

6. The apparatus of claim 1, wherein the optically transparent material is positioned in an optical window comprising a portion of the housing wall.

7. The apparatus of claim 1, wherein the housing includes a coating for reducing tissue adhesion to a housing exterior surface.

8. The apparatus of claim 7, wherein the coating comprises a corticosteroid or dexamethasone.

9. The apparatus of claim 1, wherein the power source comprises a portable battery, a lithium ion battery, a capacitor or a super capacitor.

10. The apparatus of claim 1, further comprising an induction device operably coupled to the power source for recharging the power source using an external electromagnetic signal.

11. The apparatus of claim 10, wherein the induction device comprises an induction coil.

12. The apparatus of claim 1, further comprising an RF communication device operably coupled to the processor, the RF communication device configured to generate and transmit an RF signal corresponding to the blood oxygen saturation signal.

13. The apparatus of claim 12, wherein the RF communication device sends the RF signal responsive to a signal external to the patient's body.

14. The apparatus of claim 12, wherein the RF communication device is configured to communicate with a portable monitoring device or cell phone.

15. The apparatus of claim 1, wherein the at least one wavelength comprises at least a first and a second wavelength.

16. The apparatus of claim 15, wherein the first wavelength is in a range of about 600 to about 750 nm.

17. The apparatus of claim 15, wherein the second wavelength is in a range of about 850 to about 1000 nm.

18. The apparatus of claim 1, wherein the detector comprises a photomultiplier or a charge coupled device.

19. The apparatus of claim 1, wherein the emitter is configured to emit light which penetrates at least about 1 cm into the tissue site.

20. The apparatus of claim 1, wherein the emitter is configured to emit light which penetrates at least about 2 cm into the tissue site.

21. The apparatus of claim 1, wherein the emitter comprises an LED.

22. The apparatus of claim 1, further comprising:
   a modulation device operably coupled to the detector, the modulation device configured to modulate the output signal from the detector into an electrical signal having a frequency.

23. The apparatus of claim 22, further comprising an RF communication device operably coupled to the modulation device, the RF communication device configured to transmit an RF signal corresponding to the electrical signal.

24. The apparatus of claim 1, further comprising:
   a magnetic hook coupled to the housing for removal of the apparatus from the tissue site by a removal tool containing a magnetized portion.

25. The apparatus of claim 24, wherein the magnetic hook comprises at least one of a ferrous material or a magnet.

26. The apparatus of claim 1, wherein the housing includes a biodegradable tissue penetrating attachment.

27. A system for detection of deep vein thrombosis of a patient, the system comprising:
   the apparatus of claim 1; and
   a monitoring device configured to receive an input from the apparatus and process the input into an output for indicating the presence of deep vein thrombosis.

28. The system of claim 27, wherein the monitoring device includes a display configured to display the output.

29. The system of claim 27, wherein the output is displayed on a graph.

30. The system of claim 27, wherein the apparatus wirelessly signals the input to the monitoring device.

31. A kit for detection of deep vein thrombosis of a patient, the kit comprising:
the apparatus of claim 1; and
instructions for using the apparatus of claim 1 with a portable device in order to detect deep vein thrombosis.

32. A method for measuring a blood oxygen saturation level, in a patient, the method comprising:
penetrating a hollow tissue penetrating device through a patient's skin to an intramuscular target tissue site;
injecting through the hollow tissue penetrating device to the target tissue site in the patient an apparatus for measuring blood oxygen saturation level, wherein injecting comprises applying a sufficient force on a proximal end of the housing of the apparatus to cause a distal end of the apparatus to penetrate through tissue to reach the target tissue site; and
measuring an oxygen saturation level of the target tissue site using the implanted apparatus, wherein said measuring comprises emitting light into tissue from the implanted apparatus and at least one of an intensity or wavelength of the emitted light are adjusted to penetrate a selectable depth into tissue so as to measure oxygen saturation of tissue at the selectable depth.

33. The apparatus of claim 1, where a column strength of the housing is in a range of about one to five pounds.

34. The method of claim 32, where the force applied to the proximal end of the housing is in a range of about one to five pounds.

35. An implantable apparatus for measuring blood oxygen saturation levels in a patient, the apparatus comprising:
a housing having a wall, an interior volume, an atraumatic distal end and a biodegradable tissue penetrating element attached to the atraumatic distal end of the housing so that the atraumatic distal end and the biodegradable distal end can be injected attached together into tissue, at least a portion of the housing wall comprising an optically transparent material, the housing having a size, shape and column strength to be injected through and released from a hollow tissue penetrating device into a target tissue site beneath a skin of the patient by the application of a force on a proximal end of the housing; wherein after release of the housing into tissue, the biodegradable tissue penetrating element degrades at the tissue site to reveal the atraumatic distal end of the housing;
an optical emitter positioned within the housing, the emitter arranged and configured to emit light through the housing wall and into the tissue site to measure a blood oxygen saturation within the tissue site, the emitted light having at least one wavelength whose absorbance is related to a level of blood oxygen saturation;
an optical detector positioned within the housing and arranged to receive light reflected from the tissue site, the optical detector configured to detect light at the at least one wavelength and generate a detector output signal responsive to an intensity of the detected light;
a processor positioned within the housing and operably coupled to the detector and emitter to send signals to the emitter to emit light and receive the detector output signal, the processor including logic for calculating a blood oxygen saturation level using the detector output signal and generating a signal encoding the blood oxygen saturation level; and
a power source positioned within the housing for powering at least one of the processor, the emitter or the detector, the power source coupled to at least the processor.

36. The implantable apparatus of claim 1, wherein the penetration depth of emitted light into tissue is up to about 3 cm.

37. The implantable apparatus of claim 36, wherein the penetration depth of emitted light into tissue is up to about 0.5, 1 or 2 cm.

38. An implantable apparatus for measuring blood oxygen saturation levels in a patient, the apparatus comprising:
a housing having a wall and an interior volume, at least a portion of the housing wall comprising an optically transparent material, the housing having a size, shape and column strength to be injected through and released from a hollow tissue penetrating device into an intramuscular tissue site beneath a skin of the patient by the application of a force on a proximal end of the housing;
an optical emitter positioned within the housing, the emitter arranged and configured to emit light through the housing wall and into the tissue site to measure a blood oxygen saturation within the tissue site, the emitted light having at least one wavelength whose absorbance is related to a level of blood oxygen saturation;
an optical detector positioned within the housing and arranged to receive light reflected from the tissue site, the optical detector configured to detect light at the at least one wavelength and generate a detector output signal responsive to an intensity of the detected light; wherein the optical detector and optical emitter are linearly arranged with respect to a length of the housing and recessed below the housing wall so as to produce a selected angle of light incidence and reflection with a target tissue site;
a processor positioned within the housing and operably coupled to the detector and emitter to send signals to the emitter to emit light and receive the detector output signal, the processor including logic for calculating a blood oxygen saturation level using the detector output signal and generating a signal encoding the blood oxygen saturation level; and
a power source positioned within the housing for powering at least one of the processor, the emitter or the detector, the power source coupled to at least the processor.

* * * * *